United States Patent

Hillion et al.

[11] Patent Number: 6,153,772
[45] Date of Patent: Nov. 28, 2000

[54] PROCESS FOR THE CODIMERIZATION OF POLYUNSATURATED FATTY SUBSTANCES AND OLEFINS

[75] Inventors: Gérard Hillion, Herblay; Hélène Olivier, Rueil Malmaison; Katja Siepen, La Celle Saint Cloud; Robert Stern, Paris, all of France

[73] Assignee: Institut Francais du Petrole, Rueil Malmaison Cedex, France

[21] Appl. No.: 09/121,851

[22] Filed: Jul. 24, 1998

[30] Foreign Application Priority Data

Jul. 25, 1997 [FR] France ................... 97 09615

[51] Int. Cl.[7] .................. C07C 2/08; C07C 2/38; C07B 37/02; C11C 3/12
[52] U.S. Cl. .................. 554/26; 554/124; 554/126; 554/127; 554/162; 554/224; 585/502; 585/506; 585/507
[58] Field of Search .................. 554/26, 124, 126, 554/127; 585/224, 502, 506, 507

[56] References Cited

FOREIGN PATENT DOCUMENTS 0 621 250  10/1994  European Pat. Off. .
0 621 257  10/1994  European Pat. Off. .

Primary Examiner—Joseph K. McKane
Assistant Examiner—Jane C. Osweeki
Attorney, Agent, or Firm—Millen, White, Zelano & Branigan, P.C.

[57] ABSTRACT

A cobalt catalytic system that makes it possible to obtain branched compounds from fatty substances by reacting simple olefins on polyunsaturated esters, which may or may not be conjugated, is described.

The compounds that are obtained may be hydrogenated and used as lubricant bases.

19 Claims, 4 Drawing Sheets

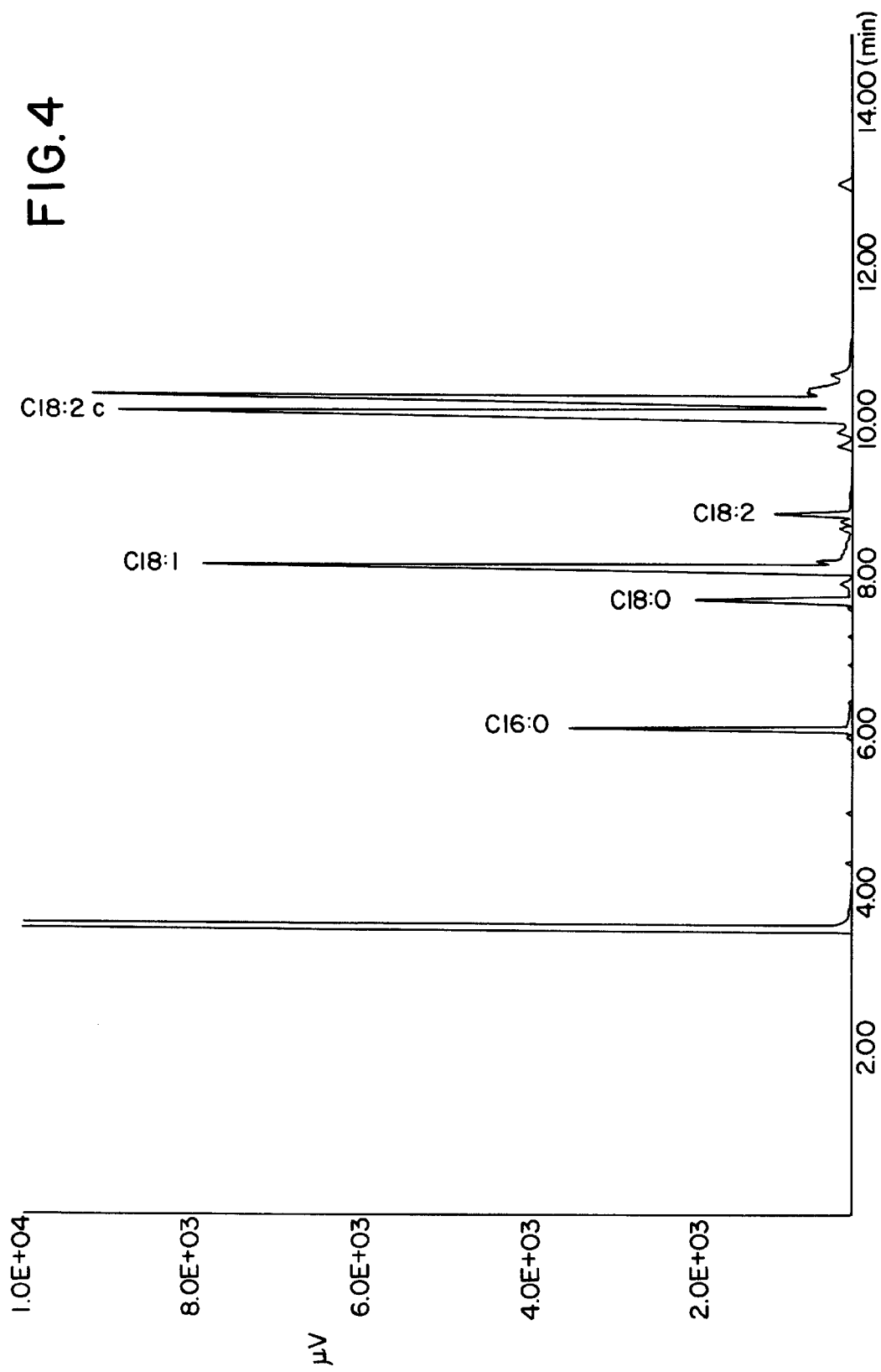

PROCESS FOR THE CODIMERIZATION OF POLYUNSATURATED FATTY SUBSTANCES AND OLEFINS

The invention has as an object a new process for obtaining chemical compounds that are derived from polyunsaturated fatty substances, whereby said compounds are characterized by the presence, along the linear hydrocarbon-containing chain, of one or more branches of at least two carbon atoms.

These compounds are obtained by adding olefins to the polyunsaturated fatty substances in the presence of a cobalt catalytic system.

These unsaturated codimers can be hydrogenated, and saturated fatty substances that are characterized by a melting point that is generally below −20° C., significant thermostability, and desired surfactant properties are then obtained. These properties are particularly advantageous in the following applications: lubricants, emulsifiers, drilling fluids, bactericides, solvents and in the form of salts for dissolving heavy metals in a polar solvents.

The reaction of olefins with butadiene or other dienes has been known for a long time and was the object of several reviews. The codimerization of butadiene with ethylene leads to hexadiene-1,4; codimerization of ethylene with isoprene to methyl-3 hexadiene; and, finally, codimerization of ethylene with piperylene produces vinyl-2-pentene. Many catalysts are used to carry out these reactions. It is possible to cite, for example, rhodium, ruthenium, palladium, cobalt, iron, or nickel systems. Systems with a titanium base have been described (Connel, Laurence G.-Ann. N.Y. Acad. Sci. (73), 214, 143–9) to catalyze the formation of vinylcyclobutane from ethylene and butadiene.

In contrast, the addition of olefin to functional dienes has rarely been described. U.S. Pat. No. 3,742,080 points out the possibility of adding ethylene to dienes, of which one or two ends of their hydrocarbon-containing chains are substituted by halogen or alkoxy groups.

It is also known that an olefin can react on a conjugated diene or triene compound according to a Diels-Alder-type reaction. For example, the addition of ethylene to the polyunsaturated fatty substances by simple heating to a temperature of 290° C. is described (R. E. Beal et Coll. JAOCS 52, 400 (1975)). Thus, a compound that has an unsaturated cycle with 6 carbon atoms in its hydrocarbon-containing chain is obtained from methyl linoleate and ethylene. After hydrogenation, these compounds have advantageous properties. Their melting point, however, which is above 10° C., is still too high to allow them to be used as lubricants.

Another method for obtaining branched compounds of fatty substances is known. It consists in reacting, according to a Wittig-type reaction, a ketone, such as, for example, the methyl ester of 12-oxo octadecanoic acid with an ylide, for example, the intermediate $P(\emptyset)_3=CHCH_3$, where $\emptyset$ represents a phenyl radical. The compound $CH_3(CH_2)_5C(=CHCH_3)(CH_3)_{10}COOCH_3$, which can be hydrogenated into methyl ethyl-12-octadecanoate, is then obtained (D. G. Chasin et Coll., Chem. Phys., Lipids (71) 6, 8–30).

In nature, the presence of branched saturated compounds of fatty substances that are found in Koch bacteria, for example, or, with another length of hydrocarbon-containing chain, in mutton fat has been pointed out.

Finally, it is known that the products that are referred to as "isostearic" contain traces of compounds that carry ethyl- or vinyl-type branches.

Recently, international patent applications WO-A-91/11427, 91-11427, 91/11426, and 91/11425 described obtaining branched fatty substance compounds by a catalytic process. The addition of olefin, such as ethylene or propylene, to the polyunsaturated fatty substance, a linoleic acid ester, for example, is catalyzed by a system with a base of rhodium, iridium, palladium, or ruthenium. The systems with rhodium, which are the only ones to have been described in an obvious way, are not very active, however.

U.S. Pat. Nos. 5,476,956 and 5,434,282 describe the use of a very specific rhodium catalytic system that makes it possible to accelerate the addition of olefin to the fatty substance dienes, particularly conjugated dienes, by a factor of 50 to 100. This process, however, is still very difficult to apply on a large scale due to excessive rhodium consumption.

The object of this invention is a new process for codimerization of a monoolefinic compound with a polyunsaturated fatty substance in the presence of a catalytic system that comprises a cobalt compound. Owing to this type of catalyst, it is possible to envision significantly reducing the cost of this reaction and also to obtain better selectivity than with the products that are obtained with the rhodium complexes.

The so-called "polyunsaturated fatty substance" compound that is employed in the reaction on which the process of the invention is based is generally a compound that comprises, on the one hand, at least two ethylene bonds, whereby these bonds can be conjugated or conjugatable two by two, and, on the other hand, a carboxylic group such as the one that is present in fatty acids that have 18 to 26 carbon atoms. Sunflower, safflower, fish, linseed, soybean, oiticica, cottonseed, colza, Chinese wood, nut, corn, linola, and grape seed oils and generally all the oils or their derived estes that comprise polyunsaturated compounds are conceivable as raw materials.

The dienic, trienic, or polyenic fatty acids that are considered can be used as such or preferably in the form of their esters that are formed either from fatty acids or oils by reaction with monofunctional alcohols, such as methanol or ethanol, difunctional alcohols, such as neopentylglycol, trifunctional alcohols such as trimethylolpropane, and polyfunctional alcohols such as sorbitol, polyglycerols, pentaerythritol and sugars. The oil itself is a possible substrate.

These esters can be totally or partially conjugated. In other words, they can contain at least two double ethylene bonds that may or may not be separated by a methylene group. Among the best-known processes for conjugating double bonds, it is possible to cite those that use alkaline alcoholates in the presence or absence of a solvent. It is possible in this case to obtain up to 99% of fatty substance that is conjugated relative to the polyunsaturated fatty substance that is initially present in the oil.

Other conjugating catalytic systems that employ ruthenium complexes or carbonyl iron are known. The cobalt system is itself conjugating. To conjugate, it is possible to attach a co-metal to it.

The monoolefinic compound that is employed in the reaction may consist of any reactive olefin that is selected from among the ordinary monoolefins (monoolefinic hydrocarbons), such as, for example, ethylene, propylene, or butene-1.

The process for preparing branched fatty substances according to the invention is characterized in that the reaction is catalyzed by a catalytic composition that comprises at least one cobalt compound, at least one reducing compound and at least one ligand containing phosphorus, arsenic, antimony or nitrogen.

The compound of cobalt may be a bivalent or a trivalent and in rare cases a monovalent inorganic or organic cobalt salt; it is possible to cite, for example, halides, thiocyanates, sulfates, nitrates, alcoholates, carbonates, carboxylates, betadiketonates or betacetocarboxylic acid esters; special examples of usable cobalt salts are cobalt (II) chloride, cobalt (III) chloride, bisacetylacetonatocobalt (II), trisacetylacetonatocobalt (III), and cobalt (II) and (III) acetates; cobalt hydroxides, organocobalt compounds and cobalt hydrides can also be used.

As reducing compounds, it is possible to cite the organoaluminum compounds of general formula $R_xAlX_{3-x}$ or $R_4Al_2SO_4$, where R is hydrogen or an alkyl group, where X is a halogen, and x=1, 2 or 3, the organic magnesium compounds of formula RMgX, where R=alkyl and X=halogen, aluminoxanes, sodium borohydride $NaBH_4$, and varied alkaline hydrides, such as $LiAlH_4$ and $NaAlH_4$ themselves or their derivatives that are obtained by substituting 1 to 3 hydrogen atoms by 1, 2 or 3 alkoxy groups, for example, $LiAlH_3(OR)$, $LiAlH_2(OR)_2$ and $LiAlH(OR)_3$, where R=alkyl group, for example, a methyl, ethyl, isopropyl, butyl, isobutyl or tert-butyl group, etc.

The ligand can be selected:
from phosphorous compounds of formula $PR_mX_{3-m}$ with m=0, 1, 2 or 3; R=aryl or alkyl; X=halogen; phosphites $P(OR)_3$, with R=aryl or alkyl; phosphine oxides $POR_3$, and diphosphines of formula $R_2P—(CH_2)_n—PR_2$, with R=aryl or alkyl and n=0–4;
from the analogous compounds of arsenic and antimony;
and from the nitrogenous ligands, such as the amide derivatives, the imines or diimines (that are produced by, for example, reaction of glyoxal with a derivative of the aniline that is substituted on the aromatic ring), and the pyridine derivatives, for example dipyridyl.

Optionally an organic compound that plays the role of a solvent can be used; as solvents, it is possible to use aliphatic or aromatic hydrocarbons, ethers, esters, halogenated hydrocarbons and, at low concentrations, sulfoxides and amides; the reaction can also be carried out without added solvent; this is then the ester, a portion of which does not react with the olefin that plays the role of solvent;

It is further possible to add to the codimerization catalyst a salt of another transition metal (for example, Fe, Ni, Cu, Rh, Pd, Mn, Mo, W or V, preferably Fe, Ni, Cu, Rh or Pd), which is introduced in a smaller proportion compared to the cobalt and which makes it possible to accelerate the reaction, in particular when the polyunsaturated substrate with a fatty substance base does not have its double bonds in conjugated form.

The molar ratio between the ligand and the cobalt compound is preferably between 0.5 and 30, in particular between 1 and 3.

If the ligand coordinates for a coordination site, it is advantageous to use it with a ligand/cobalt molar ratio that is equal to 2 to 3. If the ligand is bicoordinating, it is used with a molar ratio of 1 to 1.5.

The molar ratio between the reducing agent and the cobalt compound is generally between 1 and 30, preferably between 2 and 4.

According to this invention, it is possible to preform the catalytic system by reacting the cobalt salt, the ligand, and the reducing agent, and then introducing it into the unsaturated fatty substance in the presence of the olefin.

Generally, it is preferable to add the ligand to the cobalt compound in the presence of unsaturated fatty substance before the reducing agent is added. It is also possible to isolate a reduced complex of $CoHXL_2$-type cobalt, with X=halogen and $L_2$=a diphosphine or two phosphines and to add an alkyl aluminum or any other reducing agent in the presence of an unsaturated fatty substance.

The catalytic composition is added to the system in a catalytic quantity. This quantity is expressed as being $10^{-4}$ to $10^{-1}$ mol of cobalt per mol of conjugated unsaturated fatty substance. The reaction temperature is preferably between 50 and 120° C. The pressure of ethylene or propylene is between 0.1 and 30 MPa, preferably between 0.1 and 5 MPa. The time depends on the concentration and the nature of the catalyst. The time can be short, for example, from several minutes to several hours.

It is possible to operate according to a continuous or intermittent process. The introduction of the catalyst and esters into the reactor can be done in the presence of ethylene at low temperature or at the highest temperature directly into the reactor.

It is possible to operate with a supported, insoluble catalyst by fixing the cobalt to a polymeric, heterogeneous phosphinic substrate.

The branched fatty substances that are obtained can be hydrogenated to obtain more stable products. The hydrogenation of the olefinic compounds has been known for close to 30 years. It was carried out particularly in 1971 by Chasin, cited above. The catalysts that can be used are those that are known for hydrogenating olefins, i.e., Raney nickel, palladium on carbon, supported nickel, generally after the codimerization catalyst has been eliminated by washing with water. It is sometimes possible to use the codimerization catalyst as a hydrogenation catalyst. After hydrogenation, the unbranched saturated compounds are eliminated by crystallization or by distillation. It is also possible to distill before hydrogenation to concentrate the branched products.

The branched esters can be used as lubricating or emulsifying bases, or to undergo other treatments, such as transesterification with heavier alcohols when methyl esters are involved initially.

The entire disclosure of all applications, patents and publications, cited above and below, and of corresponding French application 97/09 615, filed Jul. 25, 1997, are hereby incorporated by reference.

BRIEF DESCRIPTION OF THE DRAWINGS

FIG. 4 is a chromatogram of a starting product.

Figure 1:
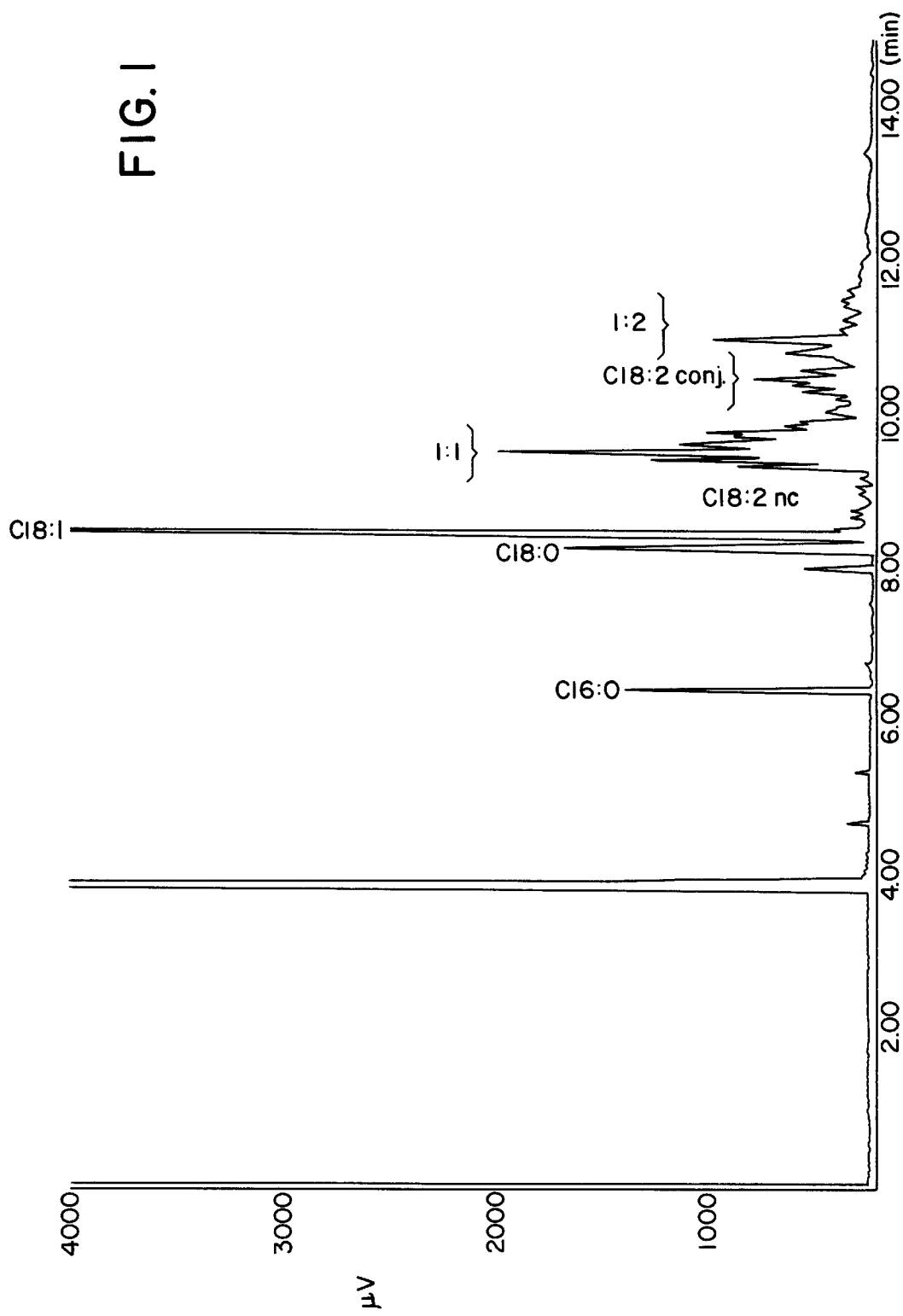
FIG. 1 is a chromatogram of reaction products.
Figure 2:
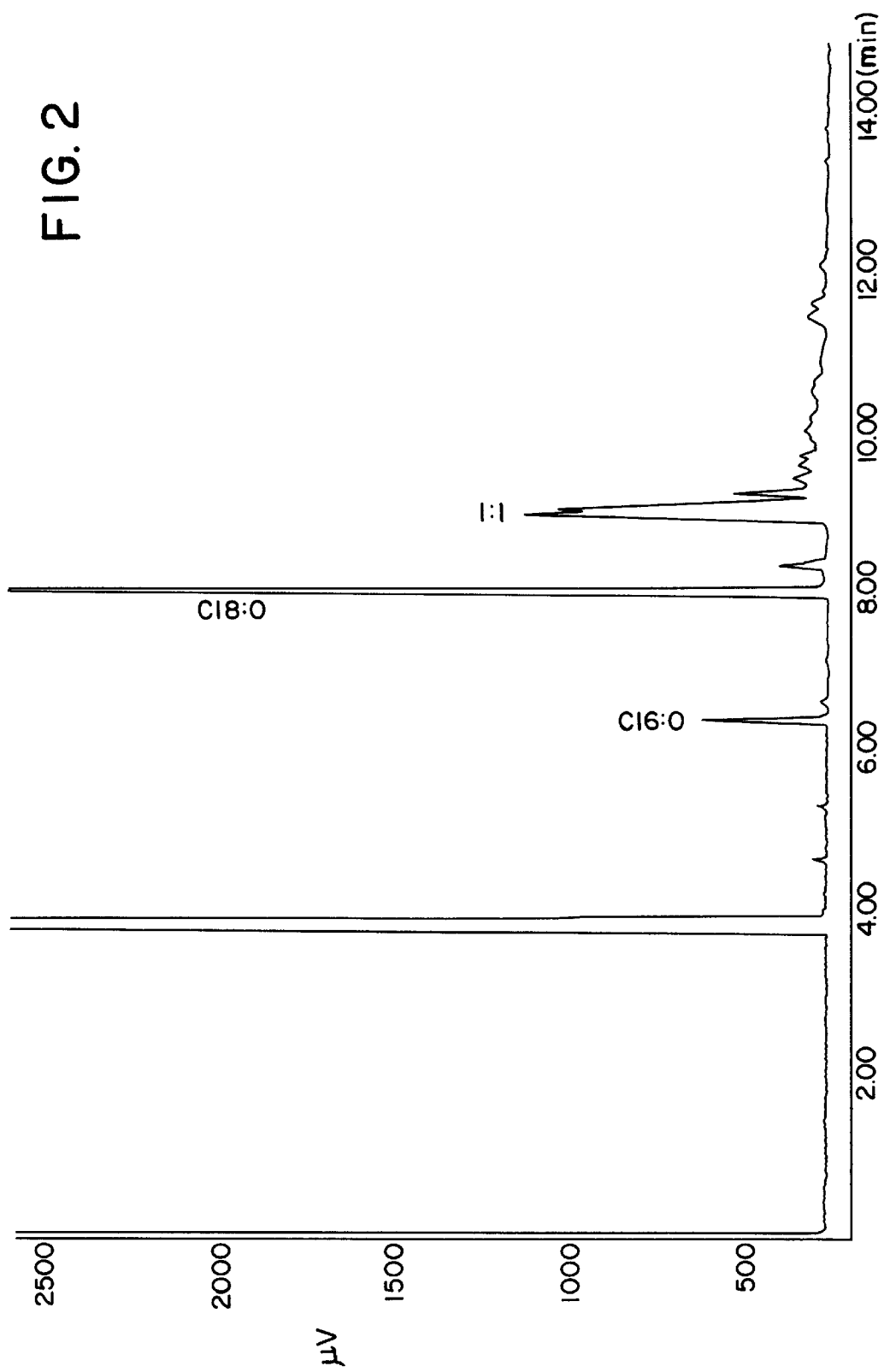
FIG. 2 is a chromatogram of a hydrogenated product.
Figure 3:
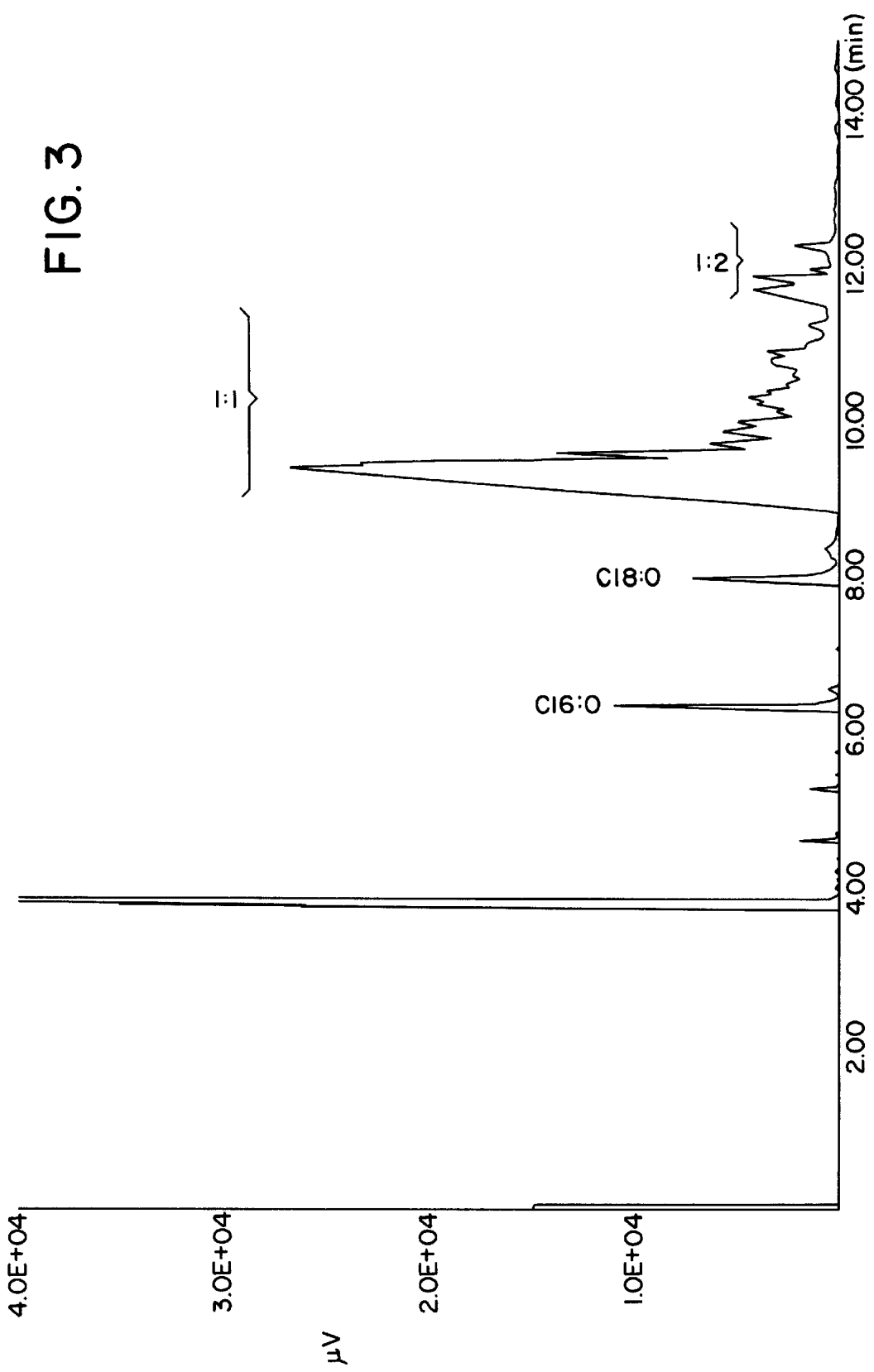
FIG. 3 is a chromatogram of the product in Example 32.

The following examples illustrate the invention; they are not limiting.

EXAMPLE 1

Preparation of the Catalyst Precursor

Introduced into a Schlenk tube, under argon atmosphere, are 1.4 mmol of bisacetylacetonatocobalt (II) $Co(acac)_2$, 1.4 mmol of diphenylphosphinoethane (dppe), 55 ml of toluene, and 30 ml of conjugated methyl ester of sunflower oil, whose composition is as follows: 4.75% of C16:0, 4.41% of C18:0, 28.5% of C18:1, 3.65% of C18:2, unconjugated, and 61.6% of C18:2, conjugated (55 mmol). This suspension is heated to 80° C. for 30 minutes, which yields a solution to which 14 mmol of diethylchloroaluminium (DEAC), 25% diluted in toluene, is added.

Codimerization Catalysis

The entire preceding solution is introduced under an argon atmosphere into a 250 ml autoclave of Hastelloy$^{(R)}$, equipped with a bar magnet stirring mechanism and a double jacket and preferably heated to 80° C. The reactor is then pressurized to 3 MPa of ethylene and is kept constant during the reaction. At the end of 3 hours, stirring is stopped, and the reactor is depressurized and opened. After the catalyst is eliminated by washing with water, the mixture that is obtained is analyzed by gas chromatography on a very polar capillary column such as BP×70 with a diameter of 0.32 cm and a length of 50 m.

EXAMPLE 2

The solution that is prepared in Example 1, but without the DEAC, is introduced into a Hastelloy$^{(R)}$ 250 ml autoclave that is preheated to 80° C. The latter (14 mmol diluted to 25% in toluene) is introduced into the reactor at 80° C. under an argon atmosphere. The reactor is then pressurized to a constant pressure of 3 MPa of ethylene. The reaction is stopped at the end of 6 hours. The results appear in Table 2. According to this table, there is no difference between these two methods of carrying out the reaction.

EXAMPLE 3

The operation is as in Example 2, but dichloro-1,2-ethane (30 ml) is used as a solvent in place of toluene. The reaction is stopped at the end of 3 hours. The results appear in Table 2.

EXAMPLE 4

The operation is as in Example 3 but without solvent. The sunflower oil methyl ester, which plays the role of solvent, has the following composition: 6.30% of C16:0, 4.72% of C18:0, 19.2% of C18:1, 5.29% of C18:2, non-conjugated, and 63.6% of C18:2, conjugated. The reaction is stopped at the end of 3 hours. The results appear in Table 2.

EXAMPLE 5

The operation is as in Example 2, but the catalytic reaction is carried out at 100° C. The reaction is stopped at the end of 3 hours. The results appear in Table 2.

EXAMPLE 6

The operation is as in Example 3, but triethylaluminum (TEA) is used instead of DEAC and is injected, undiluted, into the reactor. The sunflower oil methyl ester that is used has the same composition as the one that is described in Example 4. The reaction is stopped at the end of 3 hours. The results appear in Table 2.

EXAMPLE 7

The operation is as in Example 2, but with 1.3 mmol of dppe relative to cobalt, and the Co/AlEt$_2$Cl molar ratio= 1:10. The reaction is stopped at the end of 3 hours. The results appear in Table 2. It is noted in this test that metallic cobalt does not form.

EXAMPLE 8

The operation is as in Example 6, but toluene is used as a solvent instead of dichloro-1,2 ethane. The reaction is stopped at the end of 3 hours. The results appear in Table 2.

EXAMPLE 9

The operation is as in Example 2, but the diphenylphosphinopropane is used as a ligand instead of dppe. The reaction is stopped at the end of 4 hours. The results appear in Table 2.

EXAMPLE 10

The operation is as in Example 2, but diphenylphosphinomethane (dppm) is used as a ligand. The reaction is stopped at the end of 4 hours. The results appear in Table 2.

EXAMPLE 11

The operation is as in Example 2, but triphenylphosphine is used as a ligand. The reaction is stopped at the end of 4 hours. The results appear in Table 2.

EXAMPLE 12

The operation is as in Example 3, but CoCl$_2$ is used instead of Co(acac)$_2$. The reaction is stopped at the end of 3 and a half hours. The results appear in Table 2.

EXAMPLE 13

The operation is as in Example 2, but diphenylphopshinobutane is used instead of dppe as a ligand. The reaction is stopped after 3 hours. The results appear in Table 2.

EXAMPLE 14

The operation is as in Example 2, but cobalt triacetylacetonate is employed as a cobalt salt instead of a bivalent cobalt. After 7 hours, the results that appear in Table 2 are obtained.

EXAMPLE 15

The operation is as in Example 2, but an unconjugated ester methyl sunflower oil is used as a raw material. A portion of the linoleate conjugates, i.e., 16% of C18:2. One fraction remains in the form of C18:2 conj. (10.2%), and another fraction provides an addition product (7.7% relative to the C18:2 original).

EXAMPLE 16

The operation is as in Example 2, but the triphenylphosphine is employed as a ligand with a ligand/cobalt molar ratio=1. The results are indicated in Table 2.

EXAMPLE 17

The operation is as in Example 16, but with a ligand/cobalt molar ratio that is equal to 2. The results are indicated in Table 2.

EXAMPLE 18

The operation is as in Example 2, but cobalt chloride is used without solvent. The results are indicated in Table 2.

EXAMPLE 19

The operation is as in Example 12, but PCl, with a molar ratio Co/PCl$_3$=1.2 is used as a ligand. After 3 hours, the results indicated in Table 2 are obtained.

EXAMPLE 20

The operation is as in Example 2, except that the ligand is dicyclopentyl, 4-pyridylethylidene-phosphane ("Cytec"), with a molar ratio of 1:1 relative to cobalt.

EXAMPLE 21

In this example, conditions are used that are analogous to Example 3 with dichloroethane as a solvent and with tributylphosphine, introduced with a molar ratio 1:2 for the Co/ligand ratio, for a ligand. After 3 hours, the results obtained are indicated in Table 2.

EXAMPLE 22

The same conditions as in Example 2, except for the Co/reducing agent molar ratio=1.5, are used. The results are indicated in Table 2.

EXAMPLE 23

The conditions are identical to Example 3 except that the ligand is trimethylphosphite. The results are indicated in Table 2.

EXAMPLE 24

Here, bipyridyl is used with a Co/ligand molar ratio=1:1. The results are indicated in Table 2.

EXAMPLE 25

In this example, trioctylphosphine oxide POBu3 with a cobalt/ligand molar ratio of 1:2 is used.

EXAMPLE 26

$CoI_2$ (2.5 g) and dppe (3.2 g) in 40 ml of isopropanol, and 15 ml of ether are reacted at 30° C. It is stirred at 30° C. A blue solution is formed, which changes to green. 0.5 g of NaBH is added in powder form under nitrogen. After 30 minutes, the formation of green-yellow precipitate that is filtered and washed with ether is noted. This precipitate is dried under a vacuum at 20° C. The CoIH-dppe product formed is soluble in dichloroethane but insoluble in toluene.

The complex in the presence of $AlEt_3$, which is introduced with a molar ratio of 10 and according to the normal procedure, gives a low branched-product conversion yield of 17% considering the disappearance of $C18:2_c$, and 11% considering the formation of branched product.

EXAMPLE 27

The same CoIH-dppe complex in dichloroethane is introduced into the conjugated ester, and the diethylchloroaluminium that is used is reacted with a Co/reducing agent molar ratio of 1:10 at 80° C. for 3 hours; there is a conversion of $C18:2_c$ of 52%, and 38.8% of compound 1:1 and 1:2 appears which corresponds to 57% of the original compound $C18:2_c$. There is no black precipitate, but a green solution at the end.

EXAMPLE 28

The system that is described in Example 3 is used, except that the molar ratio between the dppe and the cobalt is 1.3, and dichloroethane is the solvent. At 80° C., after 3 hours, 65% conversion of $C18:2_c$ is obtained, and the formation of 70% of product 1:1 and 1:2 relative to the $C18:2_c$ origin is noted.

EXAMPLE 29

The same test as in Example 28 is repeated, but this time with a Co/reducing agent molar ratio of 1:4. After 2 hours, a conversion of 30.6% for $C18:2_c$ and of 32.5% of product 1:1 and 1:2 relative to theory are obtained.

EXAMPLE 30

This time, operations are carried out with the methyl ester of sunflower oil, which has the following composition:
C16:0=6.75%
C18:0=5.07%
C18:1=19.8
C18:2=68.4
$C18:2_c$=0
30 ml of ester is employed with 1.12 mmol of $Co(aca)_2$ and 0.28 mmol of $Nl(acac)_2$ in the presence of 1.4 mmol of dppe and 14 mmol of DEAC ($AlEt_2$ Cl). At 100° C. and 3 MPa of ethylene, the following are obtained after 3 hours: 50.8% of conversion of C18.2 with the formation of 20.1% of $C18:2_c$ and 27% of the addition product relative to C18:2.

EXAMPLE 31

30 ml of sunflower oil whose composition in fatty acids is given in the following table is taken. 1.12 mmol of $Co(acac)_2$, 0.28 mmol of $Ni(acac)_2$ and 1.82 mmol of dppe in toluene are added. 14 mmol of DEAC is finally added at 100° C. After 2.5 hours at 3 MPa of ethylene, a compound that is transformed into a metal ester to be able to analyze it by gas chromatography (GC) is obtained. The results are provided in Table 1 below:

TABLE 1

|  | Initial Product | Product obtained |
|---|---|---|
| C16:0 | 6.7 | 4.22 |
| C18:0 | 4.6 | 5.32 |
| C18:1 | 20.1 | 19.7 |
| C18;2 | 66.7 | 22.7 |
| $C18:2_0$ | — | 21.9 |
| 1:1 | — | 16.7 |
| 1:2 | 0 | 5.76 |
| >C18 | 1.2 | — |
| >C22 | 0 | 2.55 |

In this table,

C18:2=conjugated linoleate

1:1=addition product with 1 ethylene

1:2=addition product with 2 ethylene.

It is noted that the oil has been conjugated and that the ethylene formed two addition products.

EXAMPLE 32

After the solution of this test has been washed with water and the precipitate that forms has been filtered, the compound that is obtained in the test of Example 12 is hydrogenated without solvent with Pd/C (100 mg). After the palladium is filtered on carbon, the compound is crystallized in acetone once at 0° C. and a second time at −18° C. Vapor the addition compound remains liquid at −18° C. Vapor chromatography indicates that the compound contains 3% of C16:0, 3% of C18:0 and 94% of an addition product that is formed mainly by methyl ethyl stearate.

Nuclear magnetic resonance of the hydrogen provides a proton signal at 1.8 ppm corresponding to 1 proton on a tertiary carbon. Finally NMR of the product before hydrogenation provides several indications on the vinyl group between 4.9 and 5 ppm that was absent in the initial product and that corresponds to a double terminal bond or a compound such as methyl vinyloctadecanoate.

Table 2 below summarizes the results of Examples 1 to 25, which relate to the addition of ethylene to a methyl ester of conjugated sunflower oil. In this Table 2, the conversion of conjugated linoleates and the conversion of addition product relative to the initial conjugated ester have been considered. The catalyst is a cobalt salt that is generally reduced by $AlEt_2Cl$ in toluene, except where another solvent or another reducing agent is indicated.

TABLE 2

Addition of Ethylene to a Methyl Ester of Conjugated Sunflower Oil

| Example | Conversion of C18:2c | Conversion to Addition Product | Remarks |
|---------|----------------------|-------------------------------|---------|
| 1  | 60     | 59.0 | black ppt. |
| 2  | 62.4   | 62.4 | black ppt. |
| 3  | 70     | 75.1 | slightly black ppt. (DCE) |
| 4  | 76.0   | 70.7 | black ppt. |
| 5  | 56     | 46.6 | black ppt. |
| 6  | 73     | 65.2 | red ppt. (TEA) (DCE) |
| 7  | 64.2   | 71.5 | no ppt. |
| 8  | 31     | 21   | red ppt. (TEA) |
| 9  | 40     | 45.5 | small ppt. |
| 10 | 22     | 14.3 | black ppt. |
| 11 | 33     | 18.7 | black ppt. |
| 12 | 57     | 59   | no ppt. (DCE) |
| 13 | 17     | 5.5  | small black ppt. |
| 14 | 58     | 56.3 | black ppt. |
| 15 | 29(*)  | 7.7  | black ppt. |
| 16 | 21     | 13   | black ppt. |
| 17 | 17     | 19.4 | black ppt. |
| 18 | 70     | 64.7 | red ppt. (TEA) |
| 19 | 20     | 5.5  | no ppt., green (DCE) |
| 20 | 11     | 5.5  | black ppt. |
| 21 | 57     | 57   | small ppt., green, DCE |
| 22 | 55     | 53   | ppt. |
| 23 | 15     | 4.3  | no ppt., DCE |
| 24 | 17     | 10.1 | ppt., DCE |
| 25 | 10     | 1    | ppt., DCE |

(*)Starting point:methyl ester of the unconjugated sunflower oil, DCE=dichloroethane, TEA=triethylaluminum, ppt=precipitate.

The preceding examples can be repeated with similar success by substituting the generically or specifically described reactants and/or operating conditions of this invention for those used it he preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for obtaining a codimer, comprising reacting at least one monoolefinic compound with a fatty substance selected from the group consisting of a fatty acid comprising at least two conjugated or unconjugated ethylene bonds and an ester of said fatty acid, in the presence of a catalytic system comprising (a) at least one cobalt compound, (b) at least one reducing agent, and at least one ligand having phosphorus, arsenic, antimony or nitrogen.

2. A process according to claim 1, wherein said monoolefinic compound is ethylene, propylene, or butene-1.

3. A process according to claim 1, wherein said fatty substance that comprises at least two ethylene bonds is selected from among the dienic or polyenic fatty substances that are conjugated or are conjugatable, wherein the number of carbon atoms of the fatty chain comprises 18 to 26 carbon atoms on the chain that carries a terminal carboxylic group, with the latter group being linked as an ester to a mono, di, tri or tetrafunctional alcohol, said alcohol having a total of 1 to 18 carbon atoms.

4. A process according to claim 3, wherein the alcohol is selected from among methanol, ethanol, neopentylglycol, trimethylolpropane, 2-ethylhexanol, and glycerol.

5. A process according to claim 1, wherein the ligand is of the formula $PR_3$ or $R_2P-(CH_2)_n-PR_2$, with n=1, 2, 3 or 4 and R=alkyl or aryl, wherein the molar ratio between the cobalt and the ligand is 1 to 10.

6. A process according to claim 3, wherein the fatty substance is said ester and said ester is conjugated during the addition with said catalytic system.

7. A process according to claim 3, wherein the fatty substance is said ester and said ester is conjugated before or during the addition of olefin, with a cobalt catalyst that is cocatalyzed by traces of transition metals such as iron, nickel, copper, rhodium, or palladium.

8. A process according to claim 1, wherein the catalysts is a mixed system that is obtained by reaction of said reducing agent with $CoHXL_2$, where X is an anion, and L is a diphosphine, or an alkylphosphine.

9. A process for preparation of saturated branched compounds by hydrogenation of unsaturated branched compounds, the latter having been obtained by a process according to claim 1, said hydrogenation being conducted in the presence of the codimerization catalyst.

10. A process according to claim 9, further comprising separating the saturated branched compounds obtained by hydrogenation from residual unbranched saturated compounds.

11. A saturated branched compound that is obtained by a process according to claim 10.

12. A lubricant base, comprising a saturated branched compound according to claim 11.

13. A process according to claim 1 characterized in that, in said catalytic system:
   the cobalt compound is selected from the group consisting of the inorganic and organic cobalt salts, cobalt hydroxides, organocobalt compounds and cobalt hydrides;
   the reducing agent is an organoaluminum, an organomagnesium, an aluminoxane, a sodium borohydride or an alkali metal hydride optionally substituted by 1 to 3 alkoxy groups;
   the ligand is selected from the group consisting of:
   (a) phosphorous compounds of formula $PR_mX_{3-m}$ with m=0, 1, 2 or 3, R represents aryl or alkyl, X represents halogen;
   (b) phosphites $P(OR)_3$, R represent aryl or alkyl,
   (c) phosphine oxides $POR_3$,
   (d) diphosphines of formula $R_2P-(CH_2)_n-PR_2$, with R=aryl or alkyl and n=0–4, and the analogous compounds of arsenic and antimony, wherein the preceding ligands (a), (b), (c) and (d) are modified by the replacement of P with As or Sb; and
nitrogenous ligands selected from the group consisting of amides, imines, diimines, and pyridines.

14. A process according to claim 1, wherein said cobalt compound is a halide, acetylacetonate, or carboxylate, and said reducing agent is a substituted or unsubstituted alkylaluminum, aluminoxane, or an aluminum or boron hydride, wherein the molar ratio between the cobalt compound and the reducing agent is 1 to 30.

15. A process according to claim 3, further comprising a preceding step of conjugating said ester in the presence of an alkaline alcoholate.

16. A process according to claim 5, wherein the molar ratio is 1 to 3.

17. A process according to claim 8, wherein the anion is a halogen and L is bisphenyl phosphine.

18. A process according to claim 1, wherein said fatty substance is said fatty acid.

19. A process according to claim 1, wherein said fatty substance is said ester of said fatty acid.

* * * * *